United States Patent
Tao et al.

(10) Patent No.: US 12,286,628 B2
(45) Date of Patent: Apr. 29, 2025

(54) DIAGNOSTIC KIT FOR METASTASIS AND INVASION OF BREAST CANCER AND USE OF SHRNA MOLECULE FOR SILENCING EXPRESSION OF HUMAN LINC01614

(71) Applicant: Zhejiang Chinese Medical University, Zhejiang (CN)

(72) Inventors: Fangfang Tao, Zhejiang (CN); Zhiqian Zhang, Zhejiang (CN); Wenhong Liu, Zhejiang (CN); Ye Xu, Zhejiang (CN); Qingling Liu, Zhejiang (CN); Junfeng Li, Zhejiang (CN)

(73) Assignee: Zhejiang Chinese Medical University, Zhejiang (CN)

( * ) Notice: Subject to any disclaimer, the term of this patent is extended or adjusted under 35 U.S.C. 154(b) by 0 days.

(21) Appl. No.: 18/523,743

(22) Filed: Nov. 29, 2023

(65) Prior Publication Data

US 2024/0124880 A1    Apr. 18, 2024

Related U.S. Application Data

(62) Division of application No. 17/852,380, filed on Jun. 29, 2022, now Pat. No. 11,873,492.

(30) Foreign Application Priority Data

Dec. 8, 2021   (CN) .......................... 202111494647.0

(51) Int. Cl.
  *C12N 15/113*   (2010.01)
  *A61P 35/04*    (2006.01)
  *C12N 15/86*    (2006.01)

(52) U.S. Cl.
  CPC .......... *C12N 15/1135* (2013.01); *A61P 35/04* (2018.01); *C12N 15/86* (2013.01); *C12N 2310/14* (2013.01); *C12N 2310/531* (2013.01); *C12N 2740/15043* (2013.01)

(58) Field of Classification Search
  CPC .................................................... C12N 15/113
  See application file for complete search history.

(56) References Cited

PUBLICATIONS

Vishnubalaji et al., Long non-coding RNA (lncRNA) transcriptional landscape in breast cancer identifies LINC01614 as non-favorable prognostic biomarker regulated by TGFβ and focal adhesion kinase (FAK) signaling, Cell Death Discovery, 2019, 5: 109, pp. 1-15 (Year: 2019).*

* cited by examiner

*Primary Examiner* — Ekaterina Poliakova-Georgantas
(74) *Attorney, Agent, or Firm* — JCIPRNET

(57) ABSTRACT

The invention provides a diagnostic kit for metastasis and invasion of breast cancer and a use of an shRNA molecule for silencing expression of human LINC01614. The shRNAs obtained by the invention can interfere with the expression of LINC01614, thereby reducing the migration and invasion ability of tumor cells, inhibiting the expression of EMT proteins, and inhibiting tumor formation and lung metastasis in an animal model in vivo. The invention provides a new solution for targeted therapy of breast cancer. Therefore, the kit for diagnosing metastasis and invasion of breast cancer and the medication for treating metastasis and invasion of breast cancer are developed. The invention provides a new way and strategy for diagnosing and treating metastasis and invasion of breast cancer.

3 Claims, 6 Drawing Sheets

Specification includes a Sequence Listing.

DIAGNOSTIC KIT FOR METASTASIS AND INVASION OF BREAST CANCER AND USE OF SHRNA MOLECULE FOR SILENCING EXPRESSION OF HUMAN LINC01614

CROSS-REFERENCE TO RELATED APPLICATION

This application is a divisional application of and claims the priority benefit of U.S. application Ser. No. 17/852,380, filed on Jun. 29, 2022. The prior U.S. application Ser. No. 17/852,380 also claims the priority benefit of China application serial no. 202111494647.0, filed on Dec. 8, 2021. The entirety of each of the above-mentioned patent applications is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Nov. 28, 2023, is named 121803US-1-sequence_listing and is 12,937 bytes in size.

BACKGROUND

Technical Field

The present invention belongs to the technical field of biomedicine and mainly belongs to a medication and a diagnostic kit for inhibiting the metastasis and invasion of breast cancer.

Description of Related Art

Breast cancer is a common malignant tumor and ranks the first in female cancers due to its high incidence rate. In recent years, the female breast cancer incidence rate in China rises yearly among the younger age group. The discovery and development of anti-tumor treatment methods improve tumor patients' survival rate and life quality. However, patients receiving tumor drug treatment usually generate drug resistance, which leads to reduced curative effect, tumor recurrence and metastasis, and finally treatment failure. Invasion and metastasis of breast cancer are multi-factor and multi-step complex processes. They are regulated and controlled by the expression of multiple genes. However, the specific molecular mechanism is not completely clear at present.

LncRNAs are kind of functional RNA molecules with a length of more than 200 nt and couldn't encode proteins. It participates in regulating and controlling various biological processes in cells. At present, thousands of lncRNAs participate in regulating and controlling the expression of genes. Much research reports the abnormal expression=of lncRNAs in various malignant tumors. The influence of the abnormal expression of LncRNAs in human disease is more and more prominent. LINC01614 is a new tumor diagnosis and prognosis index. Our studies found that high expression of LINC01614 is positively correlated with multiple genes in a cell adhesion signal channel. It is also correlated with Epithelial-Mesenchymal Transition (EMT), which affects the metastasis and prognosis in various cancers. Public database mining suggested that LINC01614 is highly expressed in multiple cancers, including breast cancer, non-small cell lung cancer, gastric cancer, glioma, etc., which prompts the expression of LINC01614 is closely correlated with the occurrence and development of tumors. However, there are not many reports on LINC01614 in the literature so far.

RNA interference (RNAi) is a double-stranded RNA that mediates sequence-specific gene knockdown and widely exists in living organisms. It can be generally used in gene function exploration, infectious disease treatment, and malignant tumor treatment due to the ability to specifically knock down the expression of specific genes. The short hairpin RNA (shRNA) is a section of exogenous RNA sequence with a stem-loop structure. It can be processed into siRNAs in cells. The siRNA combined with proteins and formed an RNA-induced knockdown complex (RISC) and combined with homologous mRNAs, resulting in mRNA degradation. The shRNAs have strict targeting properties. The selection of specific target sites must match the correct position. The interference efficiency of different target sites on the same gene would be different.

In the present invention, LINC01614 specific silencing shRNAs are constructed. After transfected the shRNAs into tumor cells, the metastasis and invasion of the tumor cells were effectively inhibited, and the expression of EMT-related proteins of the tumor cells were inhibited. It provides an application basis for further in-depth exploration of the molecular mechanism of LINC01614 in breast cancer metastasis and invasion.

SUMMARY

The objective of the present invention is to design and provide a technical solution of a medication and a diagnostic kit for inhibiting metastasis and invasion of breast cancer. To achieve the above objective, the present invention adopts the following technical solution:

First, the present invention provides a kit for inhibiting metastasis and invasion of breast cancer. The kit comprises an agent for detecting an LINC01614 inhibition effect in human breast cancer cells, and the agent consists of primers shown as SEQ ID No. 10-13.

Second, the present invention provides a medication for inhibiting metastasis and invasion of breast cancer. The medication comprises shRNAs for inhibiting expression of LINC01614, wherein the shRNAs for inhibiting expression of LINC01614 comprises an shRNA-1 and/or an shRNA-2. A sense strand nucleotide sequence of the shRNA-1 is shown as SEQ ID No. 3. An antisense strand nucleotide sequence of the shRNA-1 is shown as SEQ ID No. 4. A sense strand nucleotide sequence of the shRNA-2 is shown as SEQ ID No.5. An antisense strand nucleotide sequence of the shRNA-2 is shown as SEQ ID No. 6.

Further, the medication is recombinant lentivirus expression vectors or recombinant lentiviruses that expresses the shRNAs, which could inhibit the expression of LINC01614.

Additionally, the present invention provides shRNAs for silencing the expression of LINC01614, which comprises an shRNA-1 and/or an shRNA-2. A sense strand nucleotide sequence of the shRNA-1 is shown as SEQ ID No. 3. An antisense strand nucleotide sequence of the shRNA-1 is shown as SEQ ID No. 4. A sense strand nucleotide sequence of the shRNA-2 is shown as SEQ ID No. 5. An antisense strand nucleotide sequence of the shRNA-2 is shown as SEQ ID No. 6.

Furthermore, the present invention provides an application of shRNAs for silencing expression of LINC01614 in preparation of a medication for inhibiting the expression of LINC01614.

Moreover, the present invention provides an application of shRNAs for silencing expression of LINC01614 in preparation of a medication for inhibiting metastasis and invasion of human breast cancer cells, MDA-MB-231 and Hs578T.

Finally, the present invention provides an application of shRNAs for silencing expression of LINC01614 in preparation of a medication for inhibiting metastasis and invasion of breast cancer.

The present invention has the following beneficial effects:
1, it explicitly reduces the expression of LINC01614. And it inhibits the tumor formation, metastasis and invasion ability of breast cancer, resulting in controlling breast cancer metastasis. And
2, the shRNAs are constructed on lentiviral vectors. The gene silencing is performed by transfecting breast cancer cell strains, MDA-MB-231 and Hs578T, with shRNA-lentivirus. The efficiency of gene silencing is improved. And
3, therefore, the kit for diagnosing metastasis and invasion of breast cancer and the medication for treating metastasis and invasion of breast cancer are developed, and the present invention provides a new way and strategy for the diagnosis and treatment of metastasis and invasion of breast cancer.

The shRNAs in the present invention are not reported yet. The shRNAs mentioned above can reduce the expression of LINC01614, reduce migration and invasion ability of tumor cells, inhibit the expression of EMT related protein, and inhibit tumor formation and lung metastasis in vivo. The present invention provides a new solution for targeted therapy of breast cancer.

DESCRIPTION OF THE EMBODIMENTS

Figure 1:
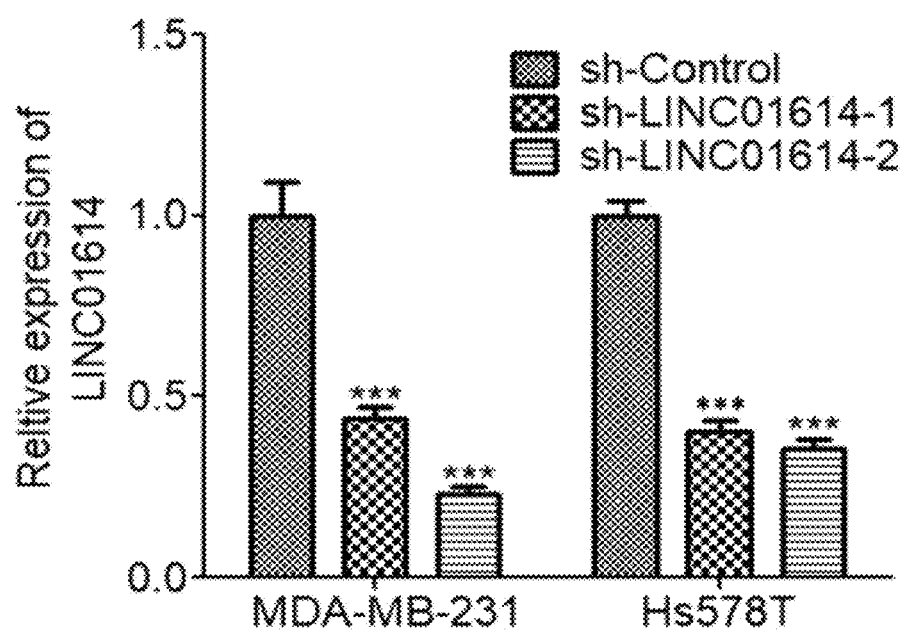
FIG. 1 shows a validation effect of lentivirus-mediated shRNAs on LINC01614 silencing in human breast cancer cells, MDA-MB-231 and Hs578T cells. * represents that compared with sh-Control, *P is less than 0.05,  P is less than 0.01, and * P is less than 0.001.

The following example illustrates the present invention but are not intended to limit the scope of the present invention. If not specifically indicated, the technical means used in the examples are conventional means well known to those skilled in the art.

Statistical Analysis

Data was subjected to statistical analysis by using SPSS 22.0 software. Measurement data was represented by mean±standard deviation. One-way ANOVA and t-test were used to examine the difference from one another among groups, and p-value less than 0.05 indicated a significant difference.

Example 1: Design of LINC01614 Specific shRNAs

The shRNA sequences were listed below:

```
shRNA-1:
                  (shown as SEQ ID No. 1)
TTCCTTAAAGTAGCAATCTTAGC;

shRNA-2:
                  (shown as SEQ ID No. 2)
GACAAGTTCAGTGGAAACTTTCT.
```

A sense strand nucleotide sequence of the shRNA-1:

```
                  (shown as SEQ ID No. 3)
5'-CCGGTTCCTTAAAGTAGCAATCTTAGCCTCGAGGCTAAGATTGCTA

CTTTAAGGAATTTTTG-3';
```

An antisense strand nucleotide sequence of the shRNA-1:

```
                  (shown as SEQ ID No. 4)
5'-AATTCAAAAATTCCTTAAAGTAGCAATCTTAGCCTCGAGGCTAAGA

TTGCTACTTTAAGGAA-3'.
```

A sense strand nucleotide sequence of the shRNA-2:

```
                  (shown as SEQ ID No. 5)
5'-CCGGGACAAGTTCAGTGGAAACTTTCTCTCGAGAGAAAGTTTCCAC

TGAACTTGTCTTTTTG-3';
```

An antisense strand nucleotide sequence of the shRNA-2:

```
                  (shown as SEQ ID No. 6)
5'-AATTCAAAAAGACAAGTTCAGTGGAAACTTTCTCTCGAGAGAAAGT

TTCCACTGAACTTGTC-3';

sh-LINC01614-1:
                  (shown as SEQ ID No. 7)
CCGGTTCCTTAAAGTAGCAATCTTAGCCTCGAGGCTAAGATTGCTACTT

TAAGGAATTTTTG;

sh-LINC01614-2:
                  (shown as SEQ ID No. 8)
CCGGGACAAGTTCAGTGGAAACTTTCTCTCGAGAGAAAGTTTCCACTGA

ACTTGTCTTTTTG.

sh-Control:
                  (shown as SEQ ID No. 9)
TTCTCCGAACGTGTCACGT.
```

Example 2: Construction of shRNA-Lentiviral Expression Vectors

The ahU6-MCS-CBh-gcGFP-IRES-puromycin vector was digested by using restriction enzymes EcoR and Age I. Digest products were separated by gel electrophoresis. Target segments were purified. Resuspending and annealing both sense and antisense shRNA oligonucleotides with the ratio of 1:1. The annealed shRNA oligonucleotides were inserted between the restriction sites in vector by ligation.

Ligation reaction was transformed into competent Escherichia coli DH5α. Candidate colonies were isolated and amplified. the shRNA inserts of the target vectors were identified by sequencing and alignment.

Table 1

Designed specific primer based on shRNA inserts

| NO. | 5' | STEM | Loop | STEM | 3' |
|---|---|---|---|---|---|
| LINC01614-1-sh1-for | Ccgg | TTCCTTAAAGTAGCAATCTTAGC | CTCGAG | GCTAAGATTGCTACTTTAAGGAA | TTTTTg |
| LINC01614-1-sh1-rev | aattcaaaaa | TTCCTTAAAGTAGCAATCTTAGC | CTCGAG | GCTAAGATTGCTACTTTAAGGAA | |
| LINC01614-1-sh2-for | Ccgg | GACAAGTTCAGTGGAAACTTTCT | CTCGAG | AGAAAGTTTCCACTGAACTTGTC | TTTTTg |
| LINC01614-1-sh2-for | aattcaaaaa | GACAAGTTCAGTGGAAACTTTCT | CTCGAG | AGAAAGTTTCCACTGAACTTGTC | |

Specific steps are as follows:

(1) Linearized and purified of the vectors. The enzyme digestion system is shown in Table 2:

TABLE 2

Enzyme digestion system

| Agent | Volume (μl) |
|---|---|
| ddH$_2$O | 41 |
| 10 × CutSmart Buffer$^2$ | 5 |
| Purified plasmid DNA (1 μg/μL) | 2 |
| Age I (10 U/μl) | 1 |
| EcoR I (10 U/μl) | 1 |
| Total | 50 |

After incubating for 1 h at 37° C. (optimum temperature), reactions were separated by electrophoresis in a 1% agarose gel. Target segments were purified and subjected to enzyme digestion.

(2) For ligation, linearization vector and annealed shRNA oligonucleotides were ligated by T4 DNA ligase at 16° C. for 1-3 h or overnight. The ligating reaction is shown in Table 3:

TABLE 3

Ligating reaction

| Agent | Volume (μl) |
|---|---|
| Linearized vector (100 ng/μL) | 1* |
| Double-stranded DNA (shRNA) (100 ng/μL) | 1 |
| 10 × T4 DNA ligase buffer | 2 |
| T4 DNA ligase | 1 |
| dd H$_2$O | Top up to 20 |

*Corresponding adjustments should be made according to the size of the vector.

(3) PCR Identification and Sequencing of Positive Transformed Colonies

Transform 50 μl competent E. coli DH5α cells with 5 μl of the ligation reaction. Leave the mixture on ice for 30 min. Heat shocks the mixture in the 42° C. bath for 90 sec then immediately incubated the mixture in the ice for 3 min. Add 950 μL of antibiotic-free liquid LB medium to the cells and incubated in 37° C. shaking incubator for 45 min with a speed of 150 rpm. Add and spread 150 μl cells suspension from each transformation on LB agar+ampicillin (100 μg/ml) plates. Incubate plates at 37° C. overnight. Pick 10 candidate isolated colonies from each transformation and inoculate each into LB+ampicillin (50-100 μg/ml). Grow overnight at 37° C. with shaking (150 RPM). The cultures were collected, and plasmid vectors were extracted. shRNA inserts were identified by sequencing and alignment. Correct aligned vectors were identified as a successfully constructed shRNA lentiviral expression vectors.

(4) Lentivirus Packaging and Titer Determination

The 293T cells were co-transfected with extracted lentivirus expression vectors and packaging plasmids (Shanghai Genechem Co., Ltd., provided a transfection agent). Harvest and filter the lentiviral supernatants through a 0.45 μm low protein binding filter to remove cellular debris within 48h. The concentrated viruses were stored at −80° C.

According to the examples, three recombinants lentivirus, sh-LINC01614-1, sh-LINC01614-2 and sh-Control were obtained.

Example 3: Transfected Human Breast Cancer Cells, MDA-MB-231 and Hs578T Cells, with sh-LINC01614-1, sh-LINC01614-2 and sh-Control Lentivirus MDA-MB-231 and Hs578T cells were prepared and inoculated to a 6-pore plate with a density of 2.5×10$^5$ cells/pore. When the cells density reached 70%, add sh-LINC01614-1, sh-LINC01614-2 or sh-Control lentivirus (MOI=10) supernatant to the cell and transduce for 24 hour. Remove and discard the lentivirus-containing transduction medium and replace with fresh growth medium. Continue to incubate the cells for 72 hours. After 72 h, the GFP expression was analysis by a fluorescence microscope. When the expression reached more than 90% indicated a successful transfection.

Example 4: Detect the Knockdown Efficiency of LINC01614 in Transfected Human Breast Cancer Cells, MDA-MB-231 and Hs578T MDA-MB-231 and Hs578T cells that transfected with sh-LINC01614-1, sh-LINC01614-2 or sh-Control lentivirus were harvested. The total RNA of each group was extracted with Total RNA extraction kit (15596026, Invitrogen Company) according to the manufacturer's instructions. The cDNAs were synthesized by reverse transcription with a reverse transcription kit (RR037A, Takara Company). The Real-time PCR detection of LINC01614 (amplification primers shown in Table 4) was performed using SYBR® Select Master Mix (Applied Biosystems, cat: 4472908) on ABI 7900 system (Applied Biosystems, Foster City, CA, USA) with the primers (Table 4) according to the manufacturer's instructions. The procedure was showed as follows: initial denaturation for 2 minutes at 94° C.; 40 cycles of denature 30 s at 94° C., anneal primers for 30 s at 55° C. and extend DNA for 1 min at 72° C. The Real-Time PCR adopted a $2^{-\Delta\Delta Ct}$ method for relative quantitative analysis.

TABLE 4

Real-time PCR Primer sequences

| Gene | Primer sequence |
|---|---|
| LINC01614F | 5'-AACCAAGAGCGAAGCCAAGA-3' (shown as SEQ ID No. 10) |
| LINC01614R | 5'-GCTTGGACACAGACCCTAGC-3' (shown as SEQ ID No. 11) |
| GAPDH F | 5'-CTGGTAAAGTGGATATTGTTGCCAT-3' (shown as SEQ ID No. 12) |
| GAPDH R | 5'-TGGAATCATATTGGAACATGTAAACC-3' (shown as SEQ ID No. 13) |

The results showed that the expression of LINC01614 in sh-LINC01614-1 group and sh-LINC01614-2 group were significantly downregulated than that of sh-Control group (P<0.001), and the silencing effect of sh-LINC01614-2 is better (shown in FIG. 1). Thus, the primers in Example 4 could be used as a kit for detecting the expression of LINC01614 in human breast cancer cells.

Example 5: Knocking Down of LINC01614 Inhibited the Clone Formation of MDA-MB-231 and Hs578T Cells MDA-MB-231 and Hs578T cells were plated in six-well plates overnight and then transfected with sh-LINC01614-1, sh-LINC01614-2 or sh-Control lentivirus. After the removal of the drug-containing medium, the cells were washed using PBS, trypsinized and plated at a low density (2000 cells/well in six-well plates). The cells were cultivated for 2-3 weeks in a humidified atmosphere containing 5% CO2 at 37° C. and the medium was refreshed every two days. Then, cells were washed with PBS for twice and fixed with 4% of paraformaldehyde for 30 minutes at room temperature and then washed with 1×PBS. Cells were stained with 0.5% crystal violet (Sigma Chemical Co, St. Louis, MO) at room temperature. The excess dye was removed by washed 3 times with distilled water. The cell colonies containing more than 50 cells were counted under microscope. Each experiment was independently repeated for 3 times.

Figure 2:
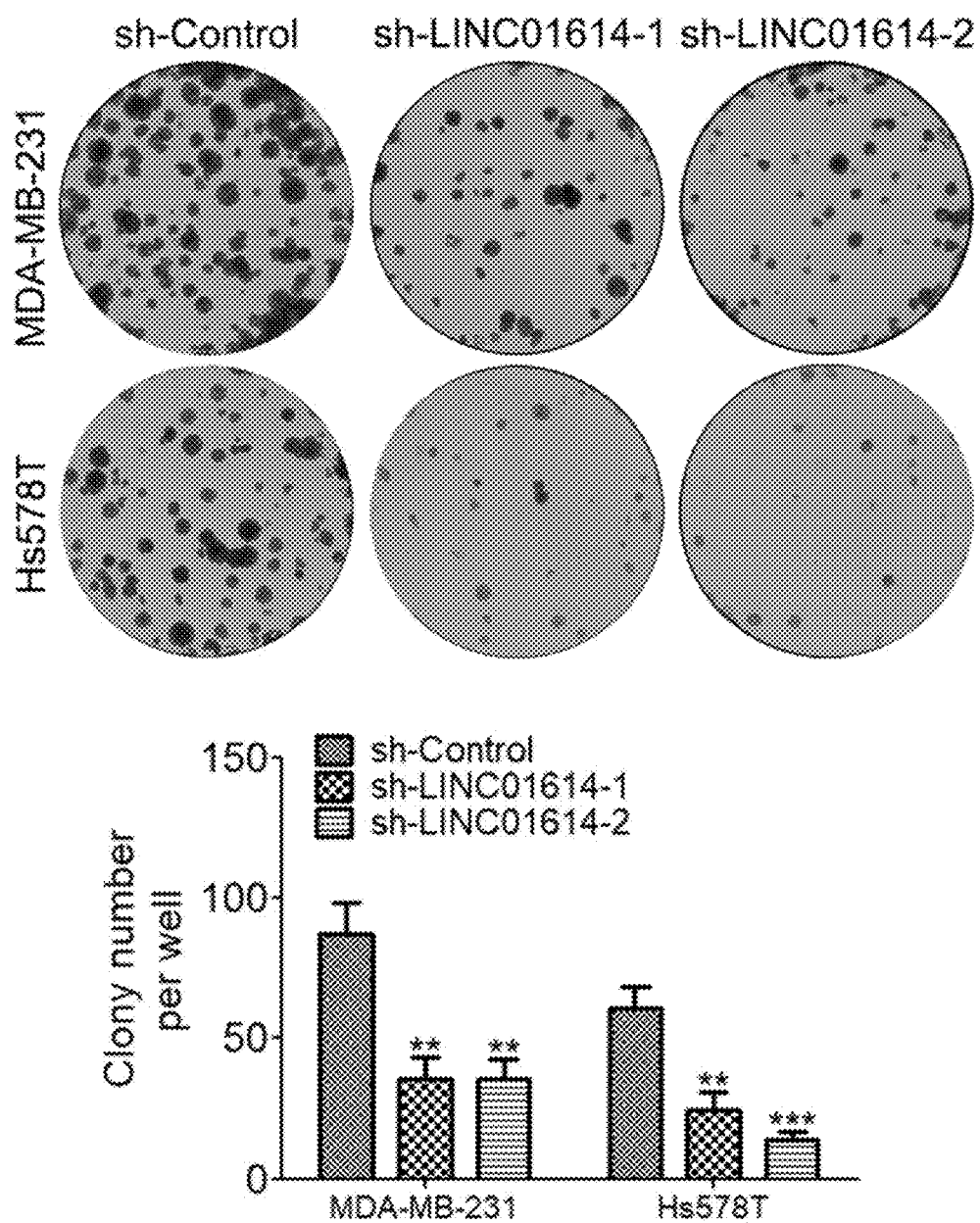
FIG. 2 shows the clone formation of MDA-MB-231 and Hs578T cells that transfected with lentivirus.

As shown in FIG. 2, the clone formation of cells that transfected by sh-LINC01614-1 and sh-LINC01614-2 were significantly reduced than that of sh-Control(P<0.01).

Example 6: Knocking Down of LINC01614 Inhibited Migration and Invasion of MDA-MB-231 and Hs578T Cells MDA-MB-231 and Hs578T cells infected with sh-LINC01614-1, sh-LINC01614-2 or sh-Control lentivirus were serum starved for 12 h and then digested with trypsin, respectively. Cells were centrifuged, diluted and resuspended with serum-free medium. For migration analysis, the transwell insert membrane is coated with Matrigel. A total of 30 µl diluted Matrigel was added to the upper chamber of each Transwell insert, which was then incubated at 37° C. for 120 min. The upper chamber of the Transwell incubated with 100 µl cells ($2×10^4$ cells/chamber) suspended in serum-free medium. The lower chamber was supplemented with 500 µl medium containing 20% FBS and incubated for 24 h at 37° C. Cells on the upper surface of the membrane were removed using a cotton swab. Cells on the bottom surface of insert membrane were fixed with 4% of paraformaldehyde for 30 minutes at room temperature and subsequently stained with 0.1% crystal violet for 30 min at room temperature. Migration cells were photographed and counted in five random fields of view under a microscope. For invasion analysis, the transwell insert membrane is NOT coated with Matrigel. The procedure is identic with the migration analysis, the only difference is WTHOUT the presence of Matrigel. Each experiment was independently repeated for 3 times.

Figure 3:
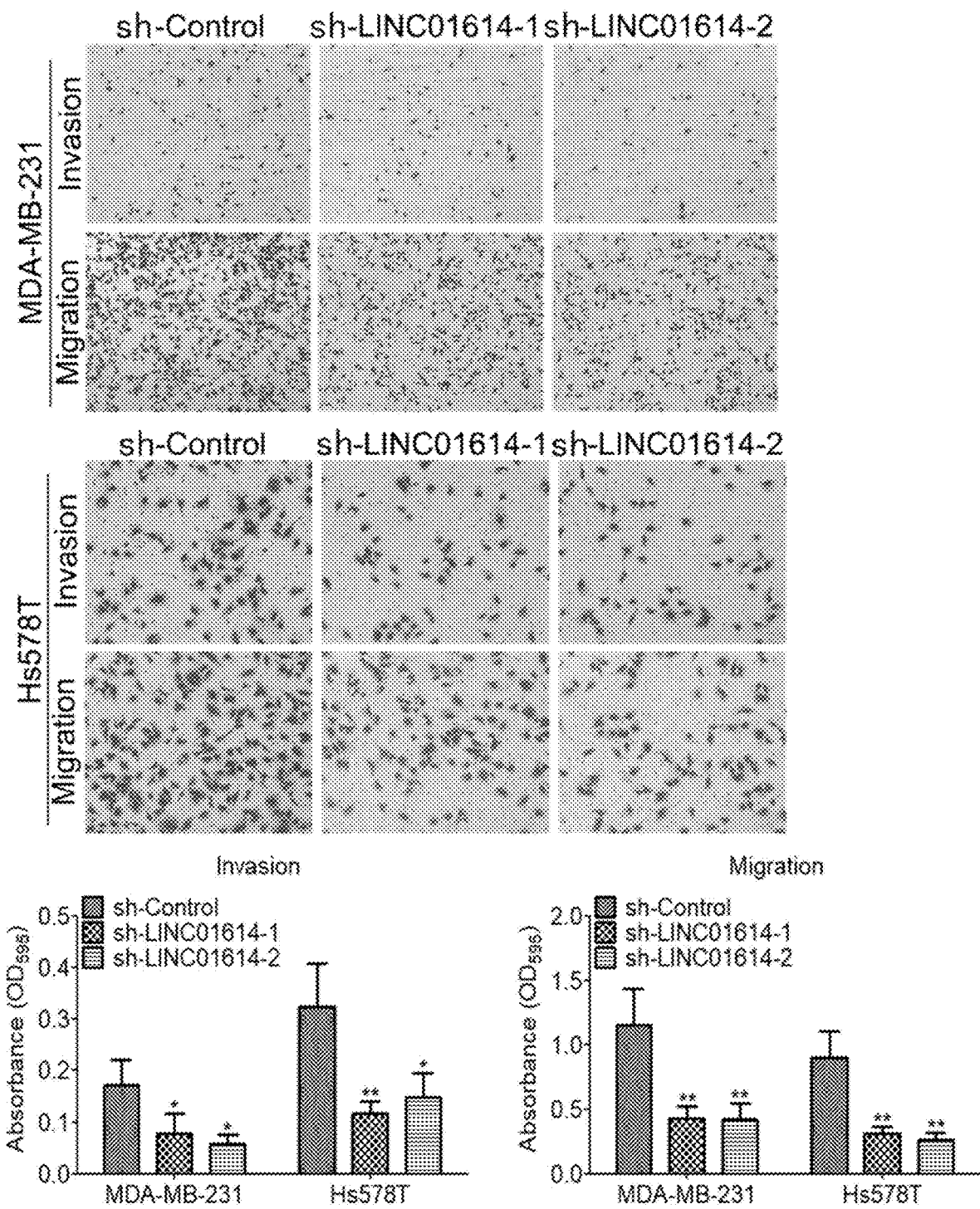
FIG. 3 shows the migration and invasion ability of MDA-MB-231 and Hs578T cells that transfected with lentivirus.

As shown in FIG. 3, the migration and invasion ability of sh-LINC01614-1 group and sh-LINC01614-2 group were significantly reduced compared with the sh-Control group (P<0.05).

Example 7: Knocking Down of LINC01614 Inhibited Epithelial-Mesenchymal Transition (EMT) of MDA-MB-231 and Hs578T Cells MDA-MB-231 and Hs578T cells infected with sh-LINC01614-1, sh-LINC01614-2 or sh-Control lentivirus. Total protein of 2×106 cells of each group were extracted using Total Protein Extraction kits (KeyGen Biotech, Nanjing, China) following the manufacturer's protocol. The protein concentration was determined by a BSA method. Equal amount of loading buffer was added and denatured at 100° C. for 10 min. 20 µg of denatured samples were loaded and separated by 12% SDS-PAGE and transferred onto a polyvinylidene difluoride (PVDF) membrane. After blocking with 5% of skimmed milk at room temperature for 1.5 h, the membrane was incubated with primary anti-rabbit E-cadherin (1:1000, CST Company) and N-cadherin (1:1000, CST Company) and rabbit anti-β-actin monoclonal antibody (1:5000, Abcam Company) at 4° C. overnight, respectively. Wash the membrane in TBST for three times, 5 min each. Then, HRP-labeled goat anti-rabbit IgG (1:5000, Abcam Company) was added and incubated at room temperature for 1h. Proteins were visualized with an enhanced chemiluminescence reagent (Wanleibio Co., Ltd.) and a Chemiluminescence Detection System (Image Lab version 5.1; Bio-Rad Laboratories, Inc.). The β-ACTIN was served as control. Each experiment was independently repeated for 3 times.

Figure 4:
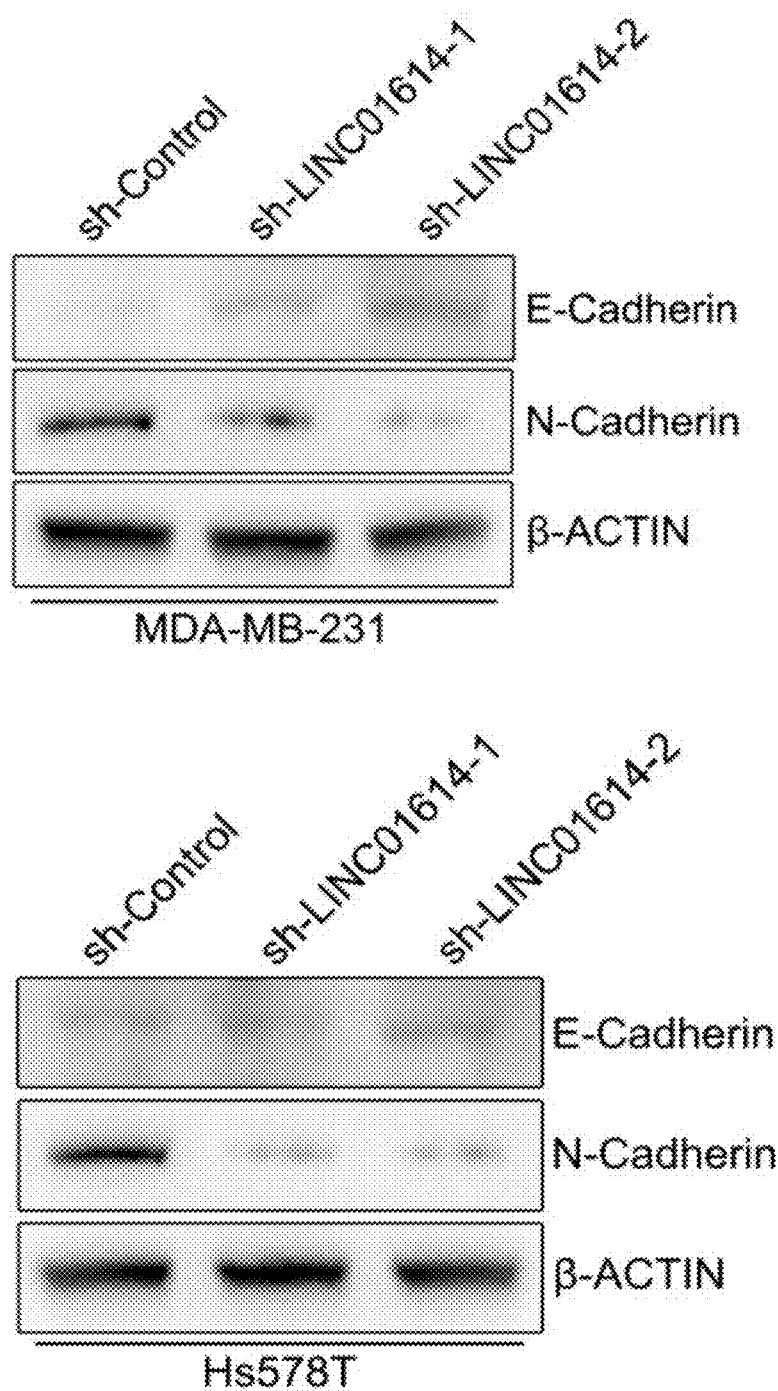
FIG. 4 shows the protein expression of EMT-related proteins, E-cadherin and N-cadherin, in MDA-MB-231 and Hs578T cells that transfected with lentivirus.

The results of western blot indicated that after knocking down of LINC01614, the expression of the EMT-related protein, E-cadherin, was increased, and the expression of the N-cadherin was reduced. These suggested that the knocking down LINC01614 could inhibit the formation of tumor cell EMT (shown as FIG. 4).

Example 8: Knocking Down of LINC01614 Inhibited the Xenograft Tumor Sizes and Lung Metastasis of MDA-MB-231 Cells For tumor xenograft mouse model, MDA-MB-231 cells transfected with sh-Control, sh-LINC01614-1, and sh-LINC01614-2 lentivirus. The BALB/c nude female mice were purchased from The Model Animal Research Center of Nanjing University (Nanjing, China). The mice were divided into three groups: sh-LINC01614-1 group, sh-LINC01614-2 group and sh-Control group. Subsequently, each 5-week-old mouse was subcutaneously injected with 1×10⁷ transfected MDA-MB-231 cells that suspended in 200 μl of PBS according to the group. The tumor sizes were monitored every 4 day. Body weight of mice also be monitored 20 days post injection. After 20 days, the nude mice were sacrificed by cervical dislocation. The long diameter (L) and the short diameter (W) of the tumor were measured. The tumor volume was calculated following the formula: (V=L×W2/2. Tumor tissue also been imaged.

For experimental lung metastasis, MDA-MB-231 cells were transinfected with sh-Control, sh-LINC01614-1, and sh-LINC01614-2 lentivirus. Transfected cells were injected into the 4- to 6-week-old BALB/c nude male mice through tail veins (5×10⁶ cells/mouse). After 4 weeks, the lung tissues were dissected and fixed in 10% formalin. Metastatic foci were counted and imaged.

Figure 5:
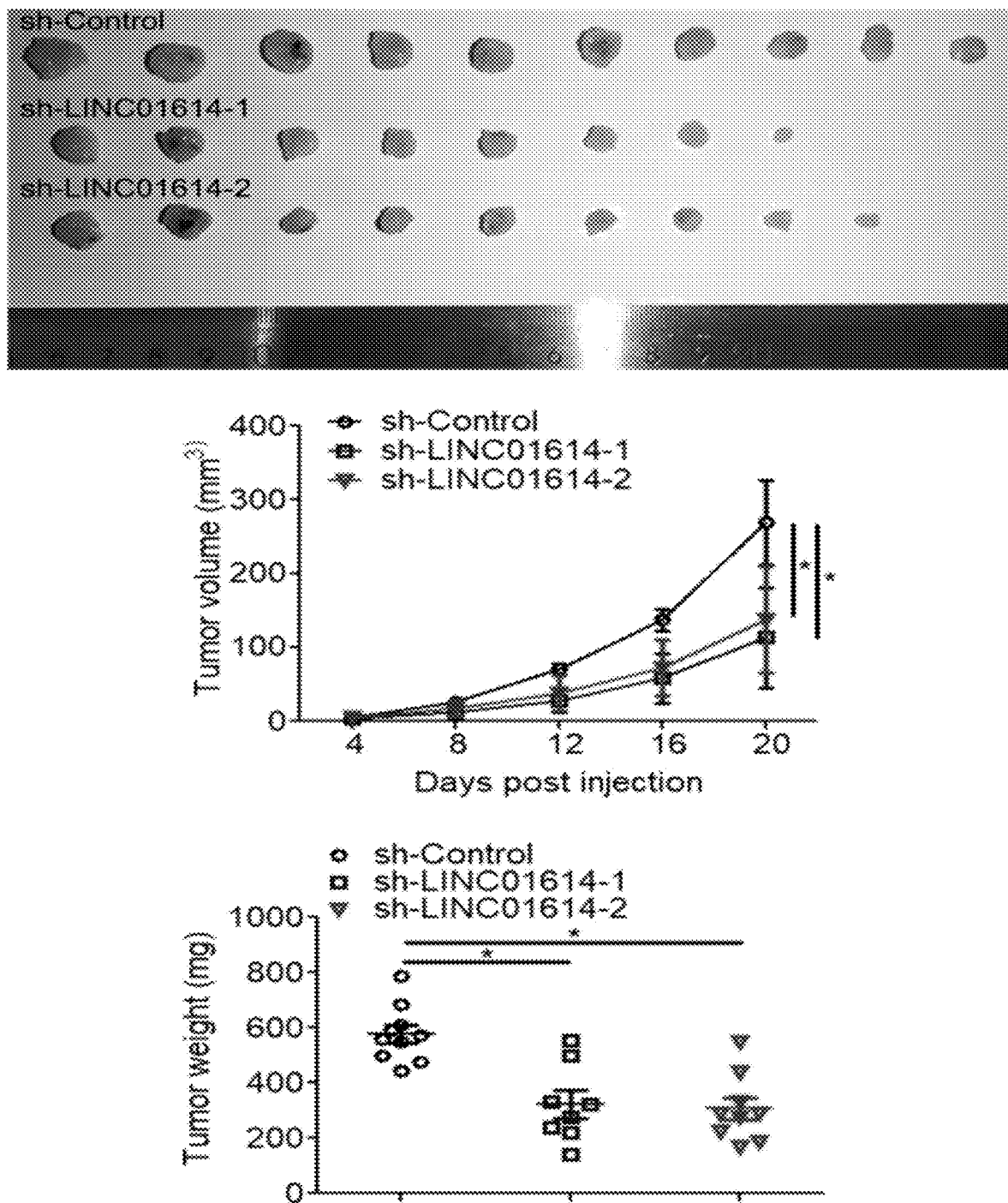
FIG. 5 shows subcutaneous tumor formation modelling of nude mice with MDA-MB-231 transfected with lentivirus to knockdown LINC01614. Tumor volume and weight were detected.
Figure 6:
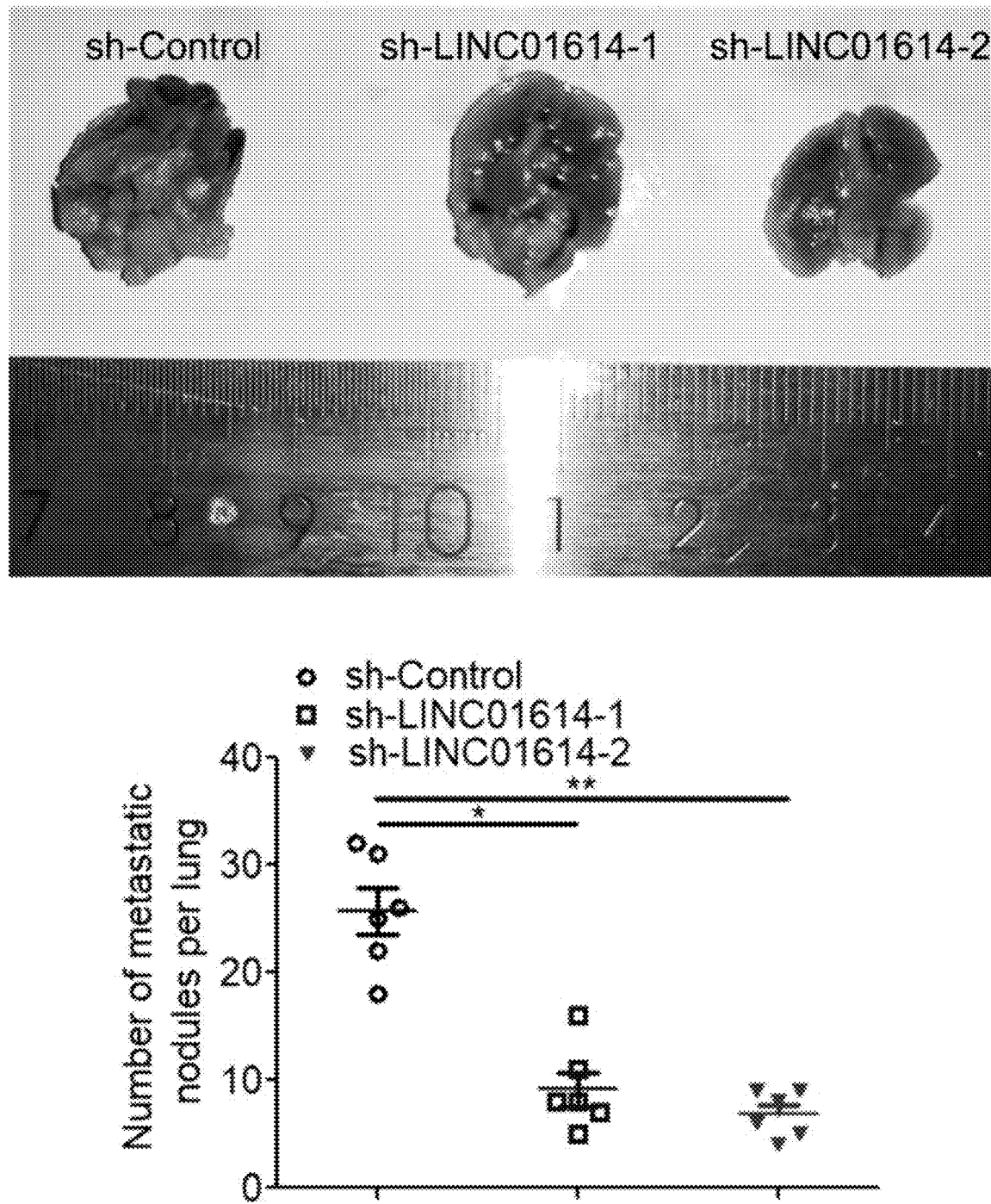
FIG. 6 shows the breast cancer lung metastasis model by tail vein injection with MDA-MB-231 transfected with lentivirus. Lung metastasis was detected.

As displayed in FIG. 5, the xenograft tumor sizes of the sh-LINC01614-1, and sh-LINC01614-2 group were significantly smaller than that of sh-Control group. As showed in FIG. 6, lung metastasis of the sh-LINC01614-1, and sh-LINC01614-2 group were reduced compared with that of sh-Control. The results indicated that downregulated of LINC01614 could significantly inhibit the MDA-MB-231 cell growth and lung metastasis in vivo.

The results of Examples 6-8 showed downregulated the expression of LINC01614 by transfection with sh-LINC01614-1, and sh-LINC01614-2 lentivirus in the present invention could be used as the medication for inhibiting metastasis and invasion of breast cancer.

The preferred examples of the present invention have been specifically described above. However, the present invention is not limited to these examples, and those skilled in the art can make various equivalents without departing from the spirit of the present invention. Modifications or substitutions of these equivalent modifications or substitutions are all included within the scope defined by the claims of the present application.

What is claimed is:

1. A method of silencing an expression of human LINC01614, comprising the following steps of
producing lentivirus having an shRNA molecule packaged within the lentivirus using a shRNA lentiviral expression vector, and
infecting the lentivirus to human breast cancer cells MDA-MB-231 and Hs578T,
wherein the shRNA molecule includes an shRNA-1 and/or an shRNA-2, and a sense strand nucleotide sequence of the shRNA-1 is shown as SEQ ID No. 3, an antisense strand nucleotide sequence of the shRNA-1 is shown as SEQ ID No. 4, a sense strand nucleotide sequence of the shRNA-2 is shown as SEQ ID No. 5, and an antisense strand nucleotide sequence of the shRNA-2 is shown as SEQ ID No. 6.

2. A method of silencing an expression of human LINC01614 for inhibiting metastasis and invasion of human breast cancer cells MDA-MB-231 and Hs578T, comprising the following steps of
transfecting an shRNA molecule to the human breast cancer cells MDA-MB-231 and Hs578T,
wherein the shRNA molecule includes an shRNA-1 and/or an shRNA-2, and a sense strand nucleotide sequence of the shRNA-1 is shown as SEQ ID No. 3, an antisense strand nucleotide sequence of the shRNA-1 is shown as SEQ ID No. 4, a sense strand nucleotide sequence of the shRNA-2 is shown as SEQ ID No. 5, and an antisense strand nucleotide sequence of the shRNA-2 is shown as SEQ ID No. 6.

3. A method of silencing an expression of human LINC01614 for inhibiting metastasis and invasion of breast cancer cell, comprising the following steps of transfecting an shRNA molecule to the breast cancer cells, wherein the shRNA molecule includes an shRNA-1 and/or an shRNA-2, and a sense strand nucleotide sequence of the shRNA-1 is shown as SEQ ID No. 3, an antisense strand nucleotide sequence of the shRNA-1 is shown as SEQ ID No. 4, a sense strand nucleotide sequence of the shRNA-2 is shown as SEQ ID No. 5, and an antisense strand nucleotide sequence of the shRNA-2 is shown as SEQ ID No. 6.

* * * * *

SEQUENCE LISTING

```
Sequence total quantity: 13
SEQ ID NO: 1            moltype = DNA  length = 23
FEATURE                 Location/Qualifiers
source                  1..23
                        mol_type = other DNA
                        organism = synthetic construct
SEQUENCE: 1
ttccttaaag tagcaatctt agc                                           23

SEQ ID NO: 2            moltype = DNA  length = 23
FEATURE                 Location/Qualifiers
source                  1..23
                        mol_type = other DNA
                        organism = synthetic construct
SEQUENCE: 2
gacaagttca gtggaaactt tct                                           23

SEQ ID NO: 3            moltype = DNA  length = 62
FEATURE                 Location/Qualifiers
source                  1..62
                        mol_type = other DNA
                        organism = synthetic construct
SEQUENCE: 3
ccggttcctt aaagtagcaa tcttagcctc gaggctaaga ttgctacttt aaggaatttt   60
tg                                                                  62

SEQ ID NO: 4            moltype = DNA  length = 62
FEATURE                 Location/Qualifiers
source                  1..62
                        mol_type = other DNA
                        organism = synthetic construct
SEQUENCE: 4
aattcaaaaa ttccttaaag tagcaatctt agcctcgagg ctaagattgc tactttaagg   60
aa                                                                  62

SEQ ID NO: 5            moltype = DNA  length = 62
FEATURE                 Location/Qualifiers
source                  1..62
                        mol_type = other DNA
                        organism = synthetic construct
SEQUENCE: 5
ccgggacaag ttcagtggaa actttctctc gagagaaagt ttccactgaa cttgtctttt   60
tg                                                                  62

SEQ ID NO: 6            moltype = DNA  length = 62
FEATURE                 Location/Qualifiers
source                  1..62
                        mol_type = other DNA
                        organism = synthetic construct
SEQUENCE: 6
aattcaaaaa gacaagttca gtggaaactt tctctcgaga gaaagtttcc actgaacttg   60
tc                                                                  62

SEQ ID NO: 7            moltype = DNA  length = 62
```

```
FEATURE              Location/Qualifiers
source               1..62
                     mol_type = other DNA
                     organism = synthetic construct
SEQUENCE: 7
ccggttcctt aaagtagcaa tcttagcctc gaggctaaga ttgctacttt aaggaatttt    60
tg                                                                   62

SEQ ID NO: 8         moltype = DNA  length = 62
FEATURE              Location/Qualifiers
source               1..62
                     mol_type = other DNA
                     organism = synthetic construct
SEQUENCE: 8
ccgggacaag ttcagtggaa actttctctc gagagaaagt ttccactgaa cttgtcttttt   60
tg                                                                   62

SEQ ID NO: 9         moltype = DNA  length = 19
FEATURE              Location/Qualifiers
source               1..19
                     mol_type = other DNA
                     organism = synthetic construct
SEQUENCE: 9
ttctccgaac gtgtcacgt                                                 19

SEQ ID NO: 10        moltype = DNA  length = 20
FEATURE              Location/Qualifiers
source               1..20
                     mol_type = other DNA
                     organism = synthetic construct
SEQUENCE: 10
aaccaagagc gaagccaaga                                                20

SEQ ID NO: 11        moltype = DNA  length = 20
FEATURE              Location/Qualifiers
source               1..20
                     mol_type = other DNA
                     organism = synthetic construct
SEQUENCE: 11
gcttggacac agaccctagc                                                20

SEQ ID NO: 12        moltype = DNA  length = 25
FEATURE              Location/Qualifiers
source               1..25
                     mol_type = other DNA
                     organism = synthetic construct
SEQUENCE: 12
ctggtaaagt ggatattgtt gccat                                          25

SEQ ID NO: 13        moltype = DNA  length = 26
FEATURE              Location/Qualifiers
source               1..26
                     mol_type = other DNA
                     organism = synthetic construct
SEQUENCE: 13
tggaatcata ttggaacatg taaacc                                         26
```